(12) United States Patent
Gonon

(10) Patent No.: US 9,095,656 B2
(45) Date of Patent: Aug. 4, 2015

(54) PULSED MEDIUM- AND HIGH-PRESSURE LIQUID JET GENERATOR FOR MEDICAL AND SURGICAL USES

(75) Inventors: Bertrand Gonon, Ternay (FR); Danièle Lesueur-Gonon, legal representative, Ternay (FR); Nicolas Gonon, legal representative, Ternay (FR)

(73) Assignee: NESTIS, Grenoble (FR)

( * ) Notice: Subject to any disclaimer, the term of this patent is extended or adjusted under 35 U.S.C. 154(b) by 0 days.

(21) Appl. No.: 13/700,167

(22) PCT Filed: May 26, 2011

(86) PCT No.: PCT/IB2011/052291
§ 371 (c)(1),
(2), (4) Date: Dec. 20, 2012

(87) PCT Pub. No.: WO2011/148333
PCT Pub. Date: Dec. 1, 2011

(65) Prior Publication Data
US 2013/0144207 A1    Jun. 6, 2013

(30) Foreign Application Priority Data

May 27, 2010   (FR) ...................................... 10 02244

(51) Int. Cl.
*A61M 5/30* (2006.01)
*A61B 17/3203* (2006.01)
*A61B 17/00* (2006.01)
*A61M 3/02* (2006.01)

(52) U.S. Cl.
CPC .............. *A61M 5/30* (2013.01); *A61B 17/3203* (2013.01); *A61M 3/0216* (2014.02); *A61M 3/0275* (2013.01); *A61B 2017/00154* (2013.01); *A61B 2217/007* (2013.01); *A61M 3/0237* (2013.01)

(58) Field of Classification Search
CPC ... A61M 5/30; A61M 3/0216; A61M 3/0237; A61M 3/0275; A61M 5/204; A61M 5/2053; A61M 5/3007; A61M 5/32; A61M 5/347; A61M 5/482; A61M 5/488; A61B 17/3203; A61B 2017/00154
USPC .......................................................... 604/70
See application file for complete search history.

(56) References Cited

U.S. PATENT DOCUMENTS

| 5,163,909 A * | 11/1992 | Stewart ........................ 604/140 |
| 5,776,104 A | 7/1998 | Guignard et al. |
| 6,083,189 A | 7/2000 | Gonon et al. |
| 2004/0097889 A1 * | 5/2004 | Pedersen et al. .............. 604/264 |

FOREIGN PATENT DOCUMENTS

| EP | 0 098 893 A1 | 1/1984 | |
| EP | 009893 A1 * | 1/1984 | ............ A61M 5/148 |
| EP | 0098893 * | 1/1984 | |
| WO | 94/28807 A1 | 12/1994 | |
| WO | 97/49441 A1 | 12/1997 | |
| WO | 02/20073 A2 | 3/2002 | |

OTHER PUBLICATIONS

International Search Report, dated Oct. 12, 2011, from corresponding PCT application.

* cited by examiner

*Primary Examiner* — Nicholas Lucchesi
*Assistant Examiner* — Diva K Chander
(74) *Attorney, Agent, or Firm* — Young & Thompson

(57) ABSTRACT

A medium- and high-pressure pulsed jet generator (1) for injecting controlled volumes of at least one medical liquid (7) includes a high-pressure chamber (2) and at least one connector (24) for at least one flexible pouch containing the medical liquid. The flexible pouch/es (6) is/are connected, via a connection tube, to a hydraulic sequencer (28) which is mounted in the high-pressure chamber, is exposed to the pressure inside the chamber (2), sequences the liquid discharged from the flexible pouch into a pulsed jet (11), is composed of a hydraulic connection (20) that is designed as or includes a deformable flexible sleeve (29) hydraulically communicating with the pouch/es (6) at the inlet and with a hand-held intervention element (40) or a catheter at the outlet, and includes hydraulic stops (31, 32) that are disposed on both sides of the flexible deformable sleeve (29) and are operated using a control element (33).

18 Claims, 2 Drawing Sheets

PULSED MEDIUM- AND HIGH-PRESSURE LIQUID JET GENERATOR FOR MEDICAL AND SURGICAL USES

BACKGROUND OF THE INVENTION

The present invention concerns a generator of medium and high-pressure liquid pulses or pulsed jets designed for various medical and surgical procedures, from a sterile dosed or undosed liquid or liquid for treatment or a dosed or undosed liquid medium containing cells or microorganisms or to implement a treatment or injection process.

More particularly, the invention concerns a generator of medium and high-pressure pulsed jets in which at least one disposable flexible bag of medical liquid is placed under controlled pressure by means of a compressed gas and in which the ejecting of the liquid from one or more flexible bags of medical liquid is pulsed and sequenced by means of a hydraulic sequencer.

The applications of this generator are multiple. They are to be found particularly but not exclusively in the fields of surgery, endoscopy and biotherapy.

DESCRIPTION OF RELATED ART

At present, the generators of high-pressure pulsed jets used in both medical and surgical fields have several applications. Several types of generators of pulsed jets are already known. Those comparable to the one of the invention comprise a flexible bag of a medical liquid placed in a pressurized enclosure, from which it emerges at a constant and controlled pressure.

The following patents US2004097889A, U.S. Pat. No. 5,776,104A, U.S. 60/831,891, U.S. Pat. No. 5,163,909A and WO9428807A describe generators of this type, in which the medical liquid under pressure goes to the outside of the enclosure into a hydraulic sequencer, forming a pulsed jet delivered by an operation handpiece.

This type of hydraulic sequencer usually is not able to create a pulsed jet having pulses of liquid in the form of perfectly square or rectangular waves, but instead creates a pulsed jet whose pressure pulses are of wave form at best pseudopulses with sloping edges. Furthermore, the pulses obtained by the pulsed jet are seldom perfectly regular and may vary in intensity or in period. This is particularly disadvantageous for certain medical or surgical applications for which the generator of pulsed jets is used for precise work dependent on the form of the pressure pulses. This is the case, in particular, in the surgical field of transmyocardial revascularization, where the form, the intensity, the duration and the periodicity of the pulses of the pressurized jet determine the size and the depth of the holes made in the wall of the heart.

SUMMARY OF THE INVENTION

The purpose of the invention is to provide a generator of pulsed jets of medium and high pressure capable of generating trains of pulsed jets formed by a succession of pressure pulses in the form of square or rectangular waves with steep edges, for which trains the intensity, the duration and the periodicity of the pressurized liquid pulses can be regulated and controlled by a generator, all the parts of which are incorporated in the high-pressure enclosure containing the liquid bags.

More particularly, the purpose of the invention is to enable a simple, rapid and dependable control of the intensity, the duration, and the periodicity of the pressurized liquid pulses in a compact generator of high-pressure pulsed jets, that is, one of reduced bulk, and a lower cost than that of the existing devices.

Advantageously, especially for reasons of modularity, versatility, and safety, such a generator of high-pressure pulsed jets enables the use of at least one flexible bag of medical liquid, and it is entirely electrically insulated, and it works equally well in pulsed and in continuous mode.

To solve these various technical problems, the generator of medium and high pressure pulsed jets according to the invention comprises the following means:

- a high-pressure enclosure, whose internal pressure is obtained from a source of pressurized gas that is regulated by a pressure control device acting on a liquid reserve present in a flexible container;
- at least one connector for flexible bags of medical liquid, each one having an interior connection conduit for the medical liquid, in fluidic communication with an outlet of a flexible bag, these connectors being provided in the high-pressure enclosure;
- a hydraulic circuit inside the enclosure, comprising in series, a conduit for connection to the flexible container, a hydraulic sequencer or modulator assembly, an outlet section of the hydraulic modulator assembly connected to an external connection conduit;
- for the feeding of a surgical instrument for work, exploration or treatment or a catheter,
- the hydraulic sequencer comprising:
  - an instantaneous dosed buffer reserve of liquid in the form of a flexible deformable envelope, in the form of a flexible tube or in the form of a compressible flexible component, bulb, balloon, or other flexible element of small capacity, mounted in series in the hydraulic connection,
  - at least one hydraulic obturating valve, but preferably two on either side of the flexible hydraulic connection, or of the compressible component, this or these hydraulic obturating valves being part of the hydraulic sequencer provided in the high pressure enclosure,
  - an alternative means of controlling the opening and closing of the hydraulic obturating valve or obturating valves;
- a means of fluid-tight connection to supply at least one operation handpiece or a catheter for operation, exploration or treatment, followed by an external connection conduit to this handpiece or this catheter.

In this device, when the enclosure is placed under high pressure, the various means that are housed therein are exposed to the high pressure. Thus, the flexible bag or bags containing the medical liquid are subjected to the pressure inside.

When the control means opens the obturating valve upstream from the hydraulic obturating valves located on the flexible hydraulic connection, the liquid coming from the flexible bag connected to this flexible hydraulic connection will fill the flexible deformable envelope.

When the control means opens the hydraulic obturating valve downstream located on the flexible hydraulic connection of the flexible deformable envelope, the liquid contained therein and possibly in the instantaneous flexible reserve is ejected and arrives under the pressure of the enclosure in the usage device, located outside the enclosure, by the external connection conduit to a handpiece or a catheter for a medical or surgical work.

The preferred use of all-or-nothing type hydraulic obturating valves makes it possible to obtain a pulsed jet formed by liquid pulses in the form of square or rectangular waves with steep edges, while the control means enables a simple, rapid and reliable control of the intensity, the duration and the periodicity of the pulses of the pressurized jets.

As the principal elements making up the invention are all housed in the same enclosure, the generator of medium and high pressure pulsed jets according to the invention has a reduced bulk. These various component elements being furthermore all subjected to the same pressure, they can be conventional components, in particular, those designed for low pressures, which reduces the cost of the generator.

Other characteristics and advantages of the invention will appear upon reading the following detailed specification, which makes reference to the appended drawings, in which:

DETAILED DESCRIPTION OF THE DRAWINGS

Figure 1:
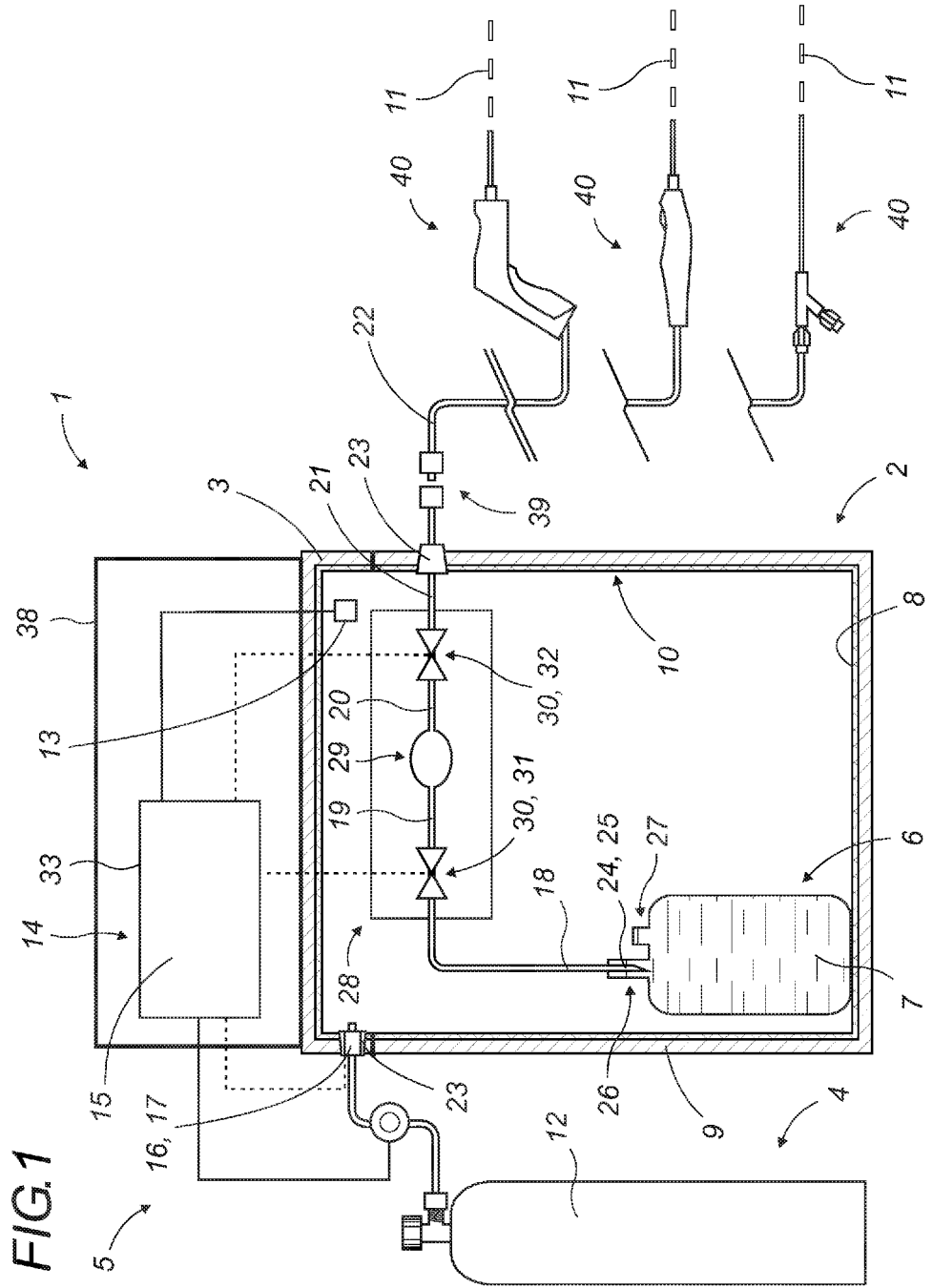
FIG. 1 is a schematic view of a generator of high-pressure pulsed jets according to a first embodiment of the invention intended for use of a single flexible bag of medical liquid.

The generator of high-pressure pulsed jets according to the present invention will now be described in detailed manner, making reference to FIGS. 1 and 2. Equivalent elements shown in the different drawings will bear the same numerical references.

In the remainder of this description the concepts of upstream and downstream will be defined on the basis of the direction of normal flow of the medical liquid or liquids used in the generator of the invention, these liquids flowing from the flexible bags to the outlet conduit after having passed through the flexible hydraulic connection and the flexible deformable envelope of the hydraulic sequencer.

The generator of high-pressure pulsed jets 1 according to the invention comprises a high-pressure enclosure 2 closed by a closure piece 3, cover, or the like, able to be opened and closed again for access to its interior. The closure piece 3 of the high-pressure enclosure 2 is preferably a cover equipped with an autoclave type seal or bearing against such a seal.

The high-pressure enclosure 2 is fluid-tight and designed to withstand high internal pressures, such as those over 50 bars, preferably those over 30 bars.

The term high pressure is relative, since it can cover a broad range of pressures from a few bars to the maximum the enclosure can withstand.

The high-pressure enclosure 2 is placed under pressure by means of a pressurization device comprising a source of a gaseous fluid under pressure 4, which supplies a preferably neutral or inert gas or sterile air under pressure, entering the high-pressure enclosure 2 to increase its internal pressure, and a pressure regulating device 5 that regulates the pressure inside the high-pressure enclosure 2.

The high-pressure enclosure 2 is fluid-tight and designed to withstand high pressures. It is preferably designed to ensure a double electrical insulation. It holds flexible bags 6 of medical liquid 7 that are electrically insulated, while a layer or plate of electrical insulator 8 is provided on or in the wall 9 of the high-pressure enclosure 2. This layer of electrical insulator 8 is preferably present on the entire internal wall 10 of the high-pressure enclosure 2.

The high-pressure enclosure 2 can be heated and thermostatically controlled, preferably to around 37° C., so that the pulsed liquid 11 produced by the generator of high-pressure pulsed jets 1 is substantially at the temperature of the human body. The regulation of this temperature is done in conventional manner, preferably by means of heating and regulation (not shown) that present no risk of soiling or contamination.

The source of pressurized gas or air 4 can come, for example, from a compressed air or gas network or a compressed gas bottle 12. The gas is preferably a sterile inert gas, chemically and biologically neutral, and respectful of the environment, or sterile air. It is preferably medical-grade nitrogen.

The pressure is measured inside the high-pressure enclosure 2 by a pressure sensor 13 connected, if necessary, to a pressure transducer and controlled by means of a control circuit 14, for example integrated in the form of an electronic card 15. The regulating of the pressure inside the high-pressure enclosure 2 is done preferably either by control of the flow rate of the pressurized gas source 4, or by control of a purge 16 making it possible to release the pressurized gas or air contained in the enclosure 2 to the outside, or by a combination of these two control techniques. The purge 16 for releasing pressurized gas contained in the enclosure 2 to the outside can take the form of opening and closing solenoid valves.

In known manner, to regulate the pressure inside the high-pressure enclosure 2 one preferably uses an integrated set 17 in the form of a block or bar and usually comprising a solenoid valve connected to a BANJO type screw, a normally open safety solenoid valve, a normally closed safety solenoid valve, a safety valve and a manometer/expansion valve.

The range of pressures commonly used in the high-pressure enclosure 2 extends preferably from 5 to 30 bars, for example, equal to or around 20 bars, for this is the zone of pressure values of a liquid jet 11 necessary for the dissection or the ablation of tissue. Of course, the person skilled in the art could use other pressures.

The pressure used in the high-pressure enclosure 2 determines the pressure of the pulsed jet 11 and thus the maximum intensity of the pulsations of the jet under pressure 11.

If need be, various hydraulic devices can be provided on the interior conduits and tubes to lower the pressure of the pulsed jet 11 coming from the generator 1.

The internal hydraulic circuit starts with the flexible bag or bags and consists of an internal connection conduit 18 going to a sequencer, an upstream tube 19 followed by a downstream tube 20 and ending up inside the enclosure by a high pressure outlet conduit 21.

The high pressure feeding of the handpiece(s) or a catheter is done by means of an external connection conduit 22.

The fluid-tightness of not only the enclosure 2 in the high pressure outlet conduit 21, but also the inlet conduit for the pressurized inert gas, is preferably ensured by sealing cone connections, such as 23, whose tapered part is directed toward the outside of the enclosure 2, so that the internal pressure of the enclosure 2 drives each cone all the more deeply, for a proportionately increased fluid-tightness.

The generator of high pressure pulsed jets 1 according to the invention also comprises at least one connector 24, each one equipped with a sterile striker 25 in fluidic communication by the internal connection conduit 18 with one of the outlets 26 of one of the flexible bags 6. The internal connection conduit 18 following each connector 24 is likewise connected to the upstream tube 19. The strikers 25 are made, for example, in the form of a PVC needle, which engages in one of the outlets 26 of the flexible bags 6 of medical type special liquid 7 usually provided for this purpose.

In fact, the flexible bags 6 of medical liquid 7 usually have at least one outlet 26 provided for perfusions, which will be used here for the connecting of the bag 6 to the rest of the device, and one inlet 27 provided for the injecting of another liquid into the bag 6, which could be used, for example, for the adding of another medical liquid 7 or for modifying the dosage of the one already present in the flexible bag 6.

These connectors 24 of flexible bags 6 can also be in the form of a very easy to use locking device, making it possible to connect a flexible bag 6 of medical liquid 7 to the rest of the device.

Each connector 24 for flexible bag 6 can be individual. There can be multiple connectors integrated in a shared assembly making it possible to connect at least one flexible bag 6 of medical liquid to a hydraulic sequencer in the high-pressure enclosure 2.

The medical liquid contained in the flexible bag or bags can be physiological fluid, serum, but also a medical liquid containing a suspension of cells, retroviruses, plasmids or any other biological or pharmaceutical agent, or a working liquid, a treatment liquid, or a liquid needed for irrigation or an exploration. It can also be electrolytes or a mixture of various liquids.

These flexible bags 6 are preferably placed in upright position in the high-pressure enclosure 2, their outlets 26 directed toward the top, so that the first cycles of use of the generator 1 of liquid pulses of the invention purge any air still present in the flexible bags 6, these first cycles of use also making it possible to perform a rinsing of the system for more safety prior to its medical or surgical use on a patient.

If the flexible bag or bags 6 of medical liquid 7 cannot stand up by themselves in the high-pressure enclosure 2, whether due to its narrowness or the holding provided by the connectors 24 for the flexible bag 6, one can provide an individual or common stand (not shown) for the flexible bags 6 that holds them in upright position, their outlets 26 pointing upward. Such a stand also makes it possible to hold the flexible bags 6 in place during movements of the generator of high pressure pulsed jets 1 of the invention.

According to another variant (not shown) of the invention, one can also consider placing the flexible bags 6 of medical liquid 7 upside down, for example, by hanging them from a hook in the upper part of the high-pressure enclosure 2, as is known to be done for perfusions.

The heart of the generator of high-pressure pulsed jets 1 according to the invention is a hydraulic sequencer 28, comprising:

a flexible deformable envelope or container 29 housed in the high-pressure enclosure 2 and exposed to the internal pressure in the enclosure or a simple piece of flexible tube, preferably easily compressible, at least one, but preferably and optionally two controlled hydraulic obturating means such as 30, where if there are two, one on each side, namely, inlet side and outlet side, or on either side of the flexible envelope that is hydraulically connected to both of them, or are present at each end of the compressible flexible tube, an alternate and cadenced means of control of the various hydraulic obturating valves, such as 30.

an upstream hydraulic obturating valve 31 housed in the high-pressure enclosure 2 and provided between the end of the internal connection conduit 18 and the upstream tube 19. This upstream hydraulic obturating valve 31 can be eliminated or replaced by a check valve or a controlled valve or the like, as will be seen hereafter or in a very simplified version be eliminated;

a downstream hydraulic obturating valve 32, housed in the high-pressure enclosure 2 and provided downstream from the flexible deformable envelope 29 and the downstream tube 20 before the outlet conduit 21; and a control assembly 33 acting on the hydraulic obturating valves 31 and 32 in cadenced and ordered fashion.

The flexible deformable envelope or the flexible deformable container 29 can be of various types with enlargement to constitute an additional capacity or a reserve.

First of all, it can involve a projecting flexible deformation, for example, in the form of a bulb in a tube, preferably also flexible.

It can also involve a separate flexible and deformable component or piece inserted into the hydraulic connection between the two obturating valves, such as a balloon, a bladder, a bulb, or some other similar piece. This is then mounted in series between the two upstream and downstream tubes 19 and 20, which can then be rigid or semi-rigid, or in any case less deformable than the flexible envelope 29 or equivalent or the like.

In any case, the flexible envelope 29 should be able to return to its initial form, for example, by resilience.

The hydraulic obturating valves such as 30 are two in number in the basic version.

The hydraulic obturating valves 31 and 32 can be reduced to a single one, preferably keeping the downstream one 32. They can also be replaced, each one or only a single one, by a check valve or controlled valve or by an equivalent hydraulic component. The upstream obturating valve 31 will preferably be replaced.

The internal connection conduits 18 and the inlet 19 and outlet 20 tubes of the generator of high pressure liquid pulses 1 are preferably made from a flexible plastic material for medical use, such as silicone, latex, PVC, etc.

Each internal connection conduit 18 and each tube 19, 20 of the generator of high pressure liquid pulses 1 can be a single piece or made up of several tubes or conduits joined together by appropriate connections (not shown).

Inside the high-pressure enclosure 2, for the connections of the various internal connection conduits 18 and tubes 19, 20 to each other, sterile disposable biconical end pieces are preferably used.

For obvious sanitary reasons, the various conduits 18 and tubes 19, 20 must be sterile. Disposable conduits 18 and tubes 19, 20 are preferably used, which are replaced after each use of the generator of high pressure pulsed jets 1 according to the invention.

The assembly may be replaced by a cassette that incorporates the different components and which, as it constitutes a single operating unit, is fully replaceable and interchangeable.

For the proper functioning of the generator of medium and high pressure liquid pulses 1, inside the high pressure enclosure 2, it is however preferable to use conduits 18 and tubes 19, 20 made from a material having greater rigidity than that of the flexible deformable envelope 29, especially in order to prevent a conduit 18 or tube 19, 20 located inside the high-pressure enclosure 2 from being deformed during the operation of the generator.

For the inlet conduit connected to the source of pressurized gas 4 and for the external connection conduit 22, it is possible to use conventional conduits known to the skilled person, respectively adapted to the passage of a gas under pressure and to the feeding of pressurized liquid to a handpiece.

As noted, the flexible deformable envelope 29 is presented, as an example, in the form of a flexible deformable bulb or balloon. It is preferably pre-formed so that, once partially or completely emptied of its contents, it automatically resumes its initial shape and volume, creating an aspiration effect, which makes it possible to fill it again when the hydraulic obturating valves 30 located upstream are open or automatically in the case of an upstream connection without an obturating valve.

The flexible deformable envelope 29 has a constant and dosed volume, preferably a volume between 200·l and 1 ml, this volume corresponding to the maximum quantity of liquid able to be released in each sequence of pulsed jet 11 produced by the generator of high pressure pulsed jets 1 of the invention. Depending on the application in mind, the flexible deformable envelope 29 can have a different volume, of course.

The flexible deformable envelope 29 can also be in the form of a simple section of very flexible and easily deformable tube, for example made of latex, whose volume is predetermined and corresponds to that needed for each sequence or train of pulsed jet 11 produced by the generator 1.

According to a variant of the invention, the flexible deformable envelope 29 can also have a volume greater than that corresponding to the quantity of liquid released at each sequence of pulses of pulsed jet 11 produced by the generator of medium and high pressure pulsed jets 1 of the invention. In this case, the downstream hydraulic obturating valve 32 of the hydraulic sequencer 28 acts on the outlet tube 20 of the flexible deformable envelope 29 to split up the volume of pressurized liquid contained in the flexible deformable envelope 29, this being for example into one or more quantities of liquid released in each pulse or sequence of pulses of pulsed jet 11. The duration and periodicity of the pulses of the jet under pressure 11 then depend directly on the duration and the periodicity of the opening and closing phases of the downstream hydraulic obturating valve 32 of the hydraulic sequencer 28 mounted on, or at the end of the outlet tube 20 of the flexible deformable envelope 29.

The flexible deformable envelope 29 can be removable and thus interchangeable. It must be sterile. Thus it can be disposable and replaced after each use of the generator of high pressure pulsed jets 1 of the invention or be specific to a given application. Thus, a specific flexible deformable envelope 29 with a different volume can be provided for each application in mind and be inserted in line between the hydraulic obturating valves 31 and 32 to allow injecting of a desired volume.

Figure 2:
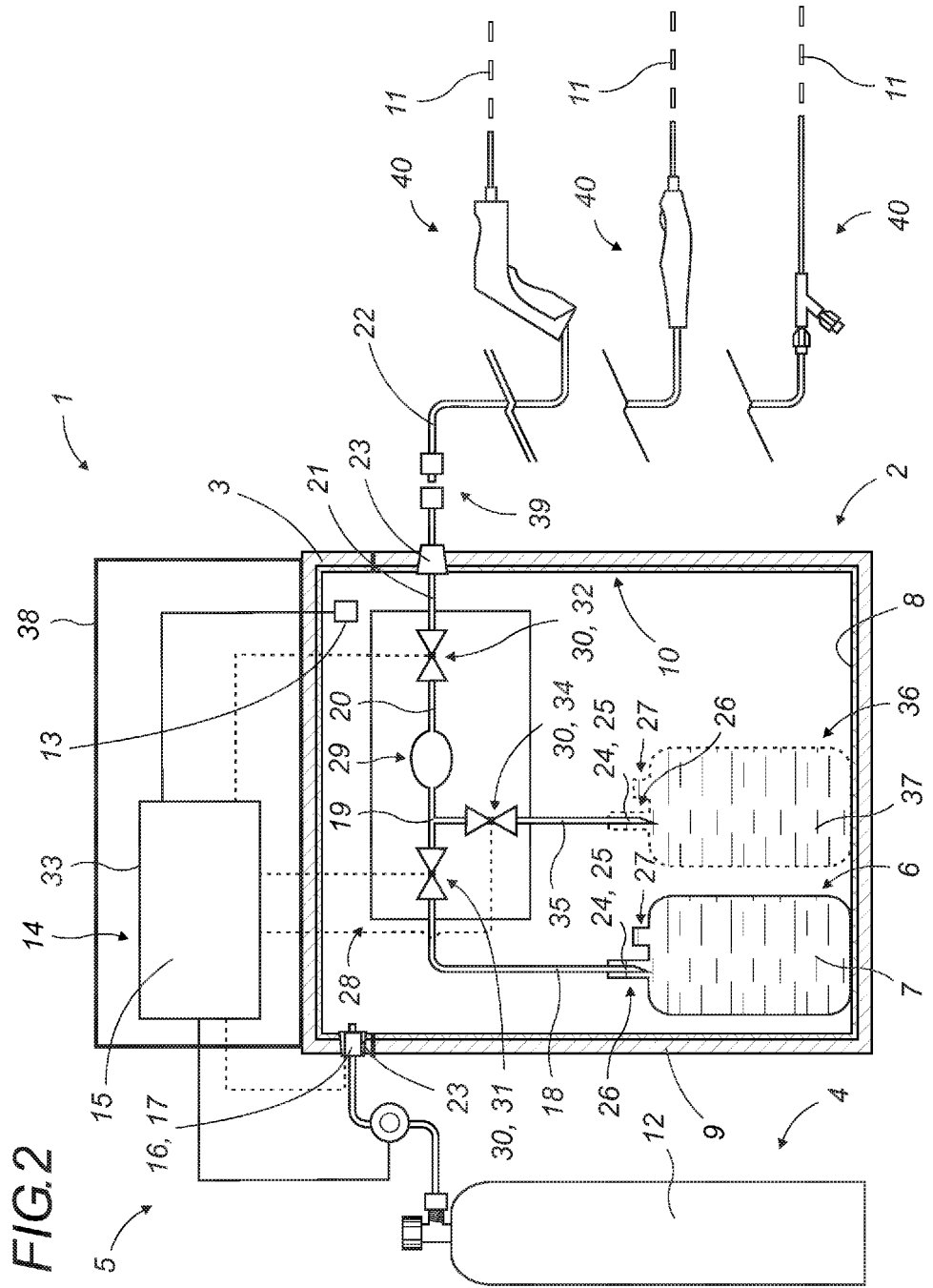
FIG. 2 is a schematic view of a generator of high-pressure pulsed jets according to a second embodiment of the invention intended for use of two flexible bags of medical liquid, the second bag being shown by broken lines, since it is optional.

An additional hydraulic obturating valve 34 can be provided upstream from the flexible deformable envelope 29, as shown in FIG. 2, this being hydraulically connected by a connection conduit 35 to a second flexible bag 36.

The group of hydraulic obturating valves is controlled by the control assembly 33.

It will be noted that the use of a second flexible bag 36 upstream from the flexible deformable envelope 29 enables injection, by the additional obturating valve 34, of a second medical liquid 37 at the same time as or alternatively to the first medical liquid 7 contained in the first flexible bag 6. The hydraulic obturating valve 34 downstream from this second bag 36 is controlled by the control means 33 to inject the second medical liquid 37 contained therein according to a precise dosage predetermined by the user.

Another additional obturating valve (not shown) can be provided upstream or downstream from the deformable envelope in order to easily isolate it, for example, so as to change or replace it.

Each hydraulic obturating valve such as 30 is preferably a mechanical element allowing alternate obturating and releasing of the obturating of the conduit 18 or tube 19, 20 on which it is mounted. These are preferably rapid hydraulic obturating valves of all-or-nothing type, for example, in the form of solenoid valves or clamping device, cam motors or other actuators that alternately clamp and release the conduits 18 and tubes 19, 20 on which they are mounted so that the resulting pulses of liquid under pressure 11 each have a square or rectangular wave signal form.

Each hydraulic obturating valve 31, 32, 34 can likewise be a solenoid valve inserted in the conduit 18 or tube 19, 20, a mechanical means of narrowing or flattening of the conduit 18 or tube 19, 20, a check valve or a controlled valve whose essential role is to prevent the return of the liquid 7 to the bag or bags 6 or 36.

In general, check valves (not shown) can be provided on the various conduits 18 and tubes 19, 20 so as to prevent any return of liquid 7 to the bag or bags 6 and any mixing of the different medical liquids 7 used.

The various means making up the hydraulic sequencer 28 are preferably mounted on a plastic insulating housing. The same is true of the control unit 33, which is protected by a housing.

The generator of high-pressure pulsed jets 1 according to the invention can also comprise at least one hydraulic connection provided in the high-pressure enclosure 2 for the connecting of one of the outlets 26 of each of the flexible bags 6 or 36 of medical liquid to the upstream inlet tube 19 of the flexible deformable envelope 29 of the hydraulic sequencer 28. This connection is preferably provided by an internal connection conduit or conduits 18 and 35 from each of the connectors 24 of each of the flexible bags 6 or 36 to the sequencer 28.

The functioning of the generator of high-pressure pulsed jets 1 according to the invention is made possible by the control means 33 for the various hydraulic obturating valves 31, 32, 34. This is preferably an electronic card, able to be programmed by the user or by a software application to control in sequential or continuous manner the opening and the closing of the different hydraulic obturating valves 31, 32, 34.

In continuous operating mode of the high-pressure generator 1 of the invention, the control means 33 controls and commands the openings and the closings of the hydraulic obturating valves and at least the movements of the upstream 31 and downstream 32 hydraulic obturating valves on either side of the flexible deformable envelope 29.

In pulsed operating mode of the generator of pulsed jets 1 of the invention, the control means 33 controls and commands the openings of at least one hydraulic obturating valve 31, 34 upstream from the flexible deformable envelope 29 and in sequenced and alternating manner the hydraulic obturating valve 32 downstream from the flexible deformable envelope 29 to enable at first the filling of the flexible deformable envelope 29 and then the generating of a pulsed liquid jet 11 dependent on the opening of the hydraulic obturating valve(s) 31 and 32, respectively upstream and downstream from the flexible deformable envelope 29.

All the possibilities of sequencing for the pulsed jet 11 can be contemplated thanks to the control means 33.

Finally, the generator of high-pressure pulsed jets 1 according to the invention also comprises a means of fluid-tight connection 39 for the connecting of the connection conduit 22 to the outlet conduit 21 of the hydraulic sequencer 28 to at least one medical or surgical operation handpiece 40, this means of fluid-tight connection 39 being provided in the wall or on the outside of the high-pressure enclosure 2.

The means of fluid-tight connection 39 for intervention hand pieces 40 is preferably a fluid-tight connection of rapid type, for example, that known as a "Luer Lock".

By operation handpiece 40 is meant any medical or surgical, endoscopic or other handpiece or tool or instrument for work or exploration, that can be connected to the outlet conduit 21 of the hydraulic sequencer 28 by an external connection conduit 22 and utilizing the high pressure pulsed jet 11. It is preferably an operation handpiece, such as a water knife, an electric knife, a catheter, or the like. Of course, it can also be an operation handpiece or an instrument having several functions.

The generator can also be connected to a simple or complex catheter which can consist of several passageways and mechanical means of operation, as well as viewing means, such as a miniature camera for exploratory work with possibility of operation or installing of prostheses or the like.

Advantageously, the control means 33 that controls the various hydraulic obturating valves such as 30 can be associated with the pressure regulating device 5 and with the temperature regulating device of the pressurized enclosure, as well as any other means making up the invention that is able to be controlled with a view to an automation and/or a regulation. Thus, all the controls and regulations of the generator of high pressure liquid pulses 1 of the invention are integrated within the same single control means 5, 33, more practical for the user, and more compact.

This single control means can be housed in the high-pressure enclosure 2 or in an external housing 38 mounted on the sealed enclosure 2 of the invention.

Also within the scope of the present invention is a simplified sequencer constituted by a very flexible calibrated tube for example a tube of silicone with a very low degree of hardness which enables efficient and fast obturations by pinching. This very flexible calibrated tube is associated with at least one obturating valve for example the downstream obturating valve which will preferably be of pinch type on this very flexible tube.

This sequencer will be slightly less precise and thus adapted for applications not requiring a precise pre-defined volume of liquid product. This type of simplified sequencer will enable a substantial saving concerning the cost of a replaceable disposable unit providing the same functions within the limit of possible technical performance.

Obviously, the invention is not limited to the preferred embodiments described above and represented in the different figures, the person skilled in the art being able to make numerous modifications to it and conceive of other variants without departing from either the scope or the context of the invention.

For example, although the various figures show each time one or two flexible bags 6 and 36, the invention can be provided to make use of a larger number, by appropriately multiplying the necessary number of elements making up the invention.

Likewise, although the invention uses only a single flexible deformable envelope 29, the person skilled in the art could easily adapt the means making up the invention to design a generator of high pressure pulsed jets 1 operating by the same principle and comprising a larger number of flexible deformable envelopes 29. This only involves a multiplication of the principal means making up the invention.

According to one variant of the invention, the hydraulic obturating valve(s) 31, 32, 34 are combined with a mechanical means of contraction on a flexible internal tube of the sequencer 28.

According to another variant of the invention not shown, it may also be envisioned to use the pressure of the pulsed liquid 11 created by the generator of medium and high pressure pulsed jets 1 for the possible driving of a mobile part of the operation handpiece 40 connected to the latter, for its cooling, its lubrication, or any other purpose.

Finally, according to another variant of the invention not shown, it may also be envisioned to use double-wall conduits and tubes in the generator of high pressure liquid pulses of the invention, for example, for the simultaneous generation of pulsed jets of two liquids or of a liquid with a gas, such as compressed air, coming from the source of sterile compressed air used to place the enclosure under high pressure, or coming from another source of compressed air.

The invention claimed is:

1. A generator of medium and high-pressure pulsed jets designed to generate high-pressure liquid pulses of at least one medical liquid contained in a flexible bag placed in a sealed high-pressure enclosure placed under medium or high pressure, having at least one outlet for liquids, the generator comprising:
    a sealed high-pressure enclosure,
    a pressurization device for the high-pressure enclosure, comprising:
    a source of gas under pressure that supplies a gas under pressure entering the high-pressure enclosure to increase its internal pressure, and
    a pressure regulating device that regulates the pressure inside the high-pressure enclosure,
    at least one connector joining a flexible bag to a connection conduit, this connector and the conduit being disposed in the high-pressure enclosure;
    and wherein the generator comprises:
    a hydraulic sequencer placed in the sealed high-pressure enclosure and comprising:
    at least one inlet where the at least one connection conduit arrives with the at least one flexible bag and an outlet communicating hydraulically with the outside of the generator,
    a flexible hydraulic connection formed by an upstream tube and a downstream tube between which is found an instantaneous dosed buffer reserve of liquid in the form of a flexible deformable envelope that is a very flexible tube of calibrated volume, the whole being exposed to the high pressure in the high-pressure enclosure,
    at least one hydraulic obturating valve in the flexible hydraulic connection;
    a means of control of the at least one hydraulic obturating valves; and
    a means of fluid-tight connection between the outlet of the hydraulic sequencer and a connection conduit with a handpiece or a catheter or an instrument for use.

2. The generator of pulsed jets according to claim 1, wherein the flexible deformable envelope is a projecting deformation of the hydraulic connection.

3. The generator of pulsed jets according to claim 1, wherein the hydraulic sequencer comprises at least one upstream hydraulic obturating valve and a downstream hydraulic obturating valve joined together by the flexible hydraulic connection.

4. The generator of pulsed jets according to claim 1, wherein the hydraulic sequencer comprises a single hydraulic obturating valve which is the downstream hydraulic obturating valve.

5. The generator of pulsed jets according to claim 1, wherein the high-pressure enclosure comprises an electrically insulating layer provided on its entire internal wall.

6. The generator of pulsed jets according to claim 1, wherein each outlet connector of each flexible bag has a sterile striker in the form of a PVC needle which engages in one of the outlets of the flexible bags of medical liquid.

7. The generator of pulsed jets according to claim 1, wherein the flexible deformable envelope is a pre-formed flexible deformable envelope with resilience of its initial shape in the form of a flexible deformable bulb or balloon.

8. The generator of pulsed jets according to claim 1, wherein each hydraulic obturating valve is a mechanical element allowing alternate obturation and releasing of the obturation of one or more tubes of the hydraulic sequencer.

9. The generator of pulsed jets according to claim 1, wherein each hydraulic obturating valve is a rapid hydraulic obturating valve of all-or-nothing type, or a solenoid valve, or a clamping device, or a cam motor, or an actuator that alternately clamps and releases the tube or tubes or a check valve or a controlled valve inserted in one of the tubes of the hydraulic sequencer.

10. The generator of pulsed jets according to claim 1, wherein the various means making up the hydraulic sequencer are mounted on a plastic insulating housing.

11. The generator of pulsed jets according to claim 1, wherein the means of control of the different hydraulic obturating valves is an electronic card able to be programmed by the user or by a software to control in sequential or continuous manner the opening and the closing of the different hydraulic obturating valves.

12. The generator of pulsed jets according to claim 1, wherein the hydraulic sequencer is formed from a very flexible calibrated tube associated with at least one obturating valve.

13. The generator of pulsed jets according to claim 12, wherein the at least one obturating valve is a mechanical means of contraction on that very flexible tube.

14. The generator of pulsed jets according to claim 13, wherein the at least one obturating valve is the downstream obturating valve.

15. The generator of pulsed jets according claim 1, wherein the hydraulic obturating valve or obturating valves is or are combined with a mechanical means of contraction on a flexible tube.

16. The generator of pulsed jets according to claim 1, wherein the high-pressure enclosure comprises means of heating and regulation.

17. A generator of medium and high-pressure pulsed jets designed to generate high-pressure liquid pulses of at least one medical liquid contained in a flexible bag placed in a sealed high-pressure enclosure placed under medium or high pressure, having at least one outlet for liquids, the generator comprising:
 a sealed high-pressure enclosure,
 a pressurization device for the high-pressure enclosure, comprising:
 a source of gas under pressure that supplies a gas under pressure entering the high-pressure enclosure to increase its internal pressure, and
 a pressure regulating device that regulates the pressure inside the high-pressure enclosure,
 at least one connector joining a flexible bag to a connection conduit, this connector and the conduit being disposed in the high-pressure enclosure;
 and wherein the generator comprises:
 a hydraulic sequencer placed in the sealed high-pressure enclosure and comprising:
 at least one inlet where the at least one connection conduit arrives with the at least one flexible bag and an outlet communicating hydraulically with the outside of the generator,
 a flexible hydraulic connection formed by an upstream tube and a downstream tube between which is found an instantaneous dosed buffer reserve of liquid in the form of a flexible deformable envelope, the whole being exposed to the high pressure in the high-pressure enclosure,
 at least one hydraulic obturating valve in the flexible hydraulic connection;
 a means of control of the at least one hydraulic obturating valves; and
 a means of fluid-tight connection between the outlet of the hydraulic sequencer and a connection conduit with a handpiece or a catheter or an instrument for use,
 wherein the conduits and the tubes located inside the high-pressure enclosure are made of a material having a greater rigidity than that of the flexible deformable envelope.

18. A generator of medium and high-pressure pulsed jets designed to generate high-pressure liquid pulses of at least one medical liquid contained in a flexible bag placed in a sealed high-pressure enclosure placed under medium or high pressure, having at least one outlet for liquids, the generator comprising:
 a sealed high-pressure enclosure,
 a pressurization device for the high-pressure enclosure, comprising:
 a source of gas under pressure that supplies a gas under pressure entering the high-pressure enclosure to increase its internal pressure, and
 a pressure regulating device that regulates the pressure inside the high-pressure enclosure,
 at least one connector joining a flexible bag to a connection conduit, this connector and the conduit being disposed in the high-pressure enclosure;
 and wherein the generator comprises:
 a hydraulic sequencer placed in the sealed high-pressure enclosure and comprising:
 at least one inlet where the at least one connection conduit arrives with the at least one flexible bag and an outlet communicating hydraulically with the outside of the generator,
 a flexible hydraulic connection formed by an upstream tube and a downstream tube between which is found an instantaneous dosed buffer reserve of liquid in the form of a flexible deformable envelope, wherein the upstream tube and the downstream tube are less deformable than the flexible deformable envelope, and the whole being exposed to the high pressure in the high-pressure enclosure,
 at least one hydraulic obturating valve in the flexible hydraulic connection;
 a means of control of the at least one hydraulic obturating valves; and
 a means of fluid-tight connection between the outlet of the hydraulic sequencer and a connection conduit with a handpiece or a catheter or an instrument for use.

* * * * *